US008083410B2

(12) United States Patent
Feist et al.

(10) Patent No.: US 8,083,410 B2
(45) Date of Patent: Dec. 27, 2011

(54) BAG WITH CLOSEABLE ACCESS ZONE

(75) Inventors: Barry Robert Feist, Madeira, OH (US); Philip Andrew Sawin, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1073 days.

(21) Appl. No.: 11/494,253

(22) Filed: Jul. 27, 2006

(65) Prior Publication Data
US 2008/0025651 A1   Jan. 31, 2008

(51) Int. Cl.
*B65D 33/24* (2006.01)
*B65D 33/16* (2006.01)

(52) U.S. Cl. .................. 383/43; 383/66; 383/99

(58) Field of Classification Search .................. 206/440, 206/494; 383/43, 66, 203, 42, 112, 87, 98, 383/99
See application file for complete search history.

(56) References Cited

U.S. PATENT DOCUMENTS

| | | | | |
|---|---|---|---|---|
| 969,954 | A * | 9/1910 | Holmes | 383/43 |
| 2,453,940 | A * | 11/1948 | Slobotkin | 383/43 |
| 2,574,345 | A * | 11/1951 | Montgomery | 206/494 |
| 2,617,573 | A * | 11/1952 | Nahoom | 224/539 |
| 3,044,517 | A * | 7/1962 | Levi | 150/158 |
| 3,109,474 | A * | 11/1963 | Levi | 150/158 |
| 4,107,364 | A | 8/1978 | Sisson | |
| 4,246,945 | A * | 1/1981 | Sterling | 383/43 |
| 4,314,558 | A * | 2/1982 | Korpman | 604/332 |
| 4,461,030 | A * | 7/1984 | Knudsen | 224/222 |
| 4,834,741 | A | 5/1989 | Sabee | |
| 4,917,267 | A * | 4/1990 | Laverdure | 222/107 |
| 4,940,464 | A | 7/1990 | Van Gompel et al. | |
| 5,092,861 | A | 3/1992 | Nomura et al. | |
| 5,143,679 | A | 9/1992 | Weber et al. | |
| 5,156,793 | A | 10/1992 | Buell et al. | |
| 5,167,897 | A | 12/1992 | Weber et al. | |
| 5,246,433 | A | 9/1993 | Hasse et al. | |
| 5,289,960 | A * | 3/1994 | Kelly et al. | 224/664 |
| 5,518,801 | A | 5/1996 | Chappell et al. | |
| 5,569,234 | A | 10/1996 | Buell et al. | |
| 5,650,214 | A | 7/1997 | Anderson et al. | |
| 5,897,545 | A | 4/1999 | Kline et al. | |
| 5,934,470 | A * | 8/1999 | Bauer et al. | 206/494 |
| 5,957,908 | A | 9/1999 | Kline et al. | |
| 5,965,182 | A * | 10/1999 | Lindgren | 426/104 |
| 5,988,468 | A * | 11/1999 | Murdoch et al. | 224/237 |
| 6,114,263 | A | 9/2000 | Benson et al. | |

(Continued)

FOREIGN PATENT DOCUMENTS

WO   WO 2006/112901 A1   10/2006

OTHER PUBLICATIONS

International Search Report.

*Primary Examiner* — Jes F Pascua
(74) *Attorney, Agent, or Firm* — George H. Leal; Laura L. Whitmer; Amy M. Foust

(57) ABSTRACT

A bag having a closeable access zone is provided. The access zone includes an access to the interior of the bag and a first portion and a second portion enabling closure of the access zone.

15 Claims, 15 Drawing Sheets

U.S. PATENT DOCUMENTS

| | | |
|---|---|---|
| 6,120,487 A | 9/2000 | Ashton |
| 6,120,489 A | 9/2000 | Johnson et al. |
| 6,605,172 B1 | 8/2003 | Anderson et al. |
| 6,926,149 B2 * | 8/2005 | Tippey .................. 206/494 |
| 7,370,760 B2 * | 5/2008 | Clough .................. 206/494 |
| 2001/0040114 A1 * | 11/2001 | Laurent .................. 206/494 |
| 2002/0088825 A1 * | 7/2002 | Laverdure .................. 222/107 |
| 2003/0215161 A1 * | 11/2003 | Rubman .................. 383/43 |
| 2003/0233082 A1 | 12/2003 | Kline et al. |
| 2005/0035150 A1 * | 2/2005 | Laverdure .................. 222/92 |
| 2005/0103667 A1 * | 5/2005 | Tippey .................. 206/440 |
| 2005/0273072 A1 | 12/2005 | Hird et al. |
| 2006/0131200 A1 | 6/2006 | Boldra et al. |
| 2006/0231448 A1 * | 10/2006 | Clough .................. 206/494 |

* cited by examiner

BAG WITH CLOSEABLE ACCESS ZONE

FIELD OF THE INVENTION

This invention relates generally to bags, and more specifically to bags including a closeable access zone.

BACKGROUND OF THE INVENTION

A broad range of consumer products are sold in bags such as plastic bags. Most typically, the bag is opened, for example by cutting or tearing, to access the interior of the bag. Generally, once the interior of the bag has been accessed, the integrity of the bag is compromised and the bag cannot be reclosed.

Diapers are an example of a product sold in a plastic bag. In order to access the interior of a bag containing diapers, the bag is typically cut or ripped such that the diapers may be removed therefrom. Frequently, once the integrity of the bag has been compromised, a consumer feels they should remove all of the diapers from the bag so that the diapers are not exposed to contaminants such as dirt that may infiltrate the access zone of the bag. Thus, the consumer will remove the diapers and place them in a secondary storage. Moreover, after the consumer has removed the diapers from the bag, the consumer typically will discard the bag.

A need exists for product bags having an access zone that is closeable to prevent infiltration of contaminants. A need also exists for a closeable bag that can be reused, rather than discarded.

SUMMARY OF THE INVENTION

Bags, and more specifically bags including a closeable access zone, are provided. The bags may be used to hold any suitable product such as a diaper, an absorbent article, a cleaning product, a beauty care product, a medical product, a medical device, a food product, or other products.

In one embodiment, a bag having a closeable access zone is provided. The access zone includes an access to the interior of the bag and a first portion and a second portion each joined to the bag enabling closure of the access. The portion enabling closure of the access comprises first and second elastic members.

In another embodiment, a bag with a closeable access zone is provided wherein the bag comprises a plastic material. An access is formed in the plastic material. An access zone is provided wherein the access zone may be opened by applying an opening force thereto. The access zone includes a closure mechanism and is self-closing once the opening force is removed.

While multiple embodiments are disclosed herein, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

DETAILED DESCRIPTION OF THE INVENTION

Figure 1:
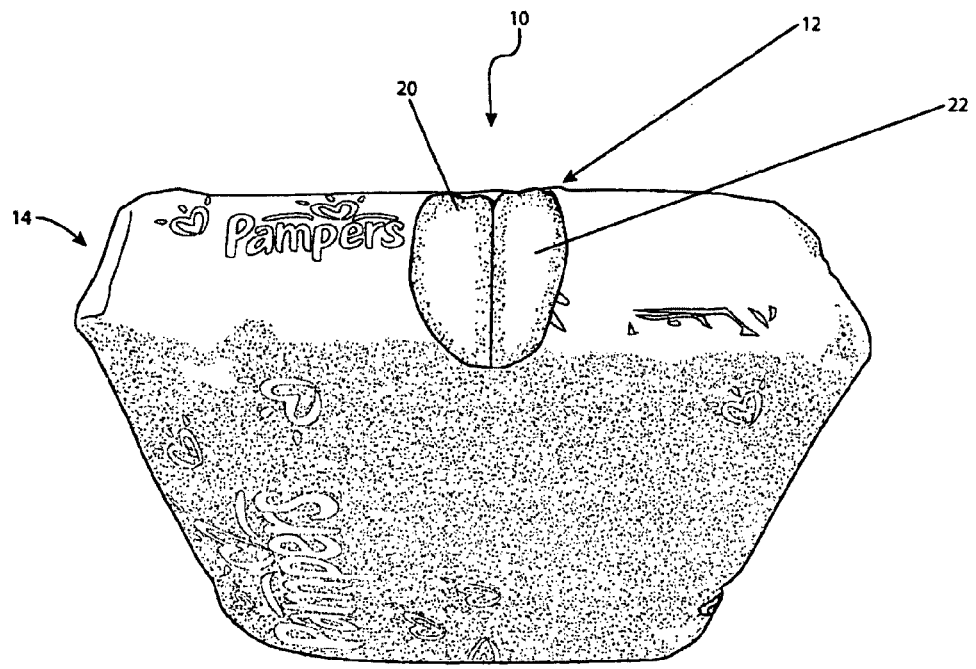
FIG. 1 illustrates a perspective view of a bag having an access zone comprising first and second overlapping portions of slow recovery elastic in accordance with one embodiment of the present invention.

Definitions:

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element. Additionally configurations where an element is permanently secured to another element or removably secured to another element are included.

The terms "pant", "training pant", "closed diaper", "prefastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

Description:

Bags, and more specifically bags including a closeable access zone, are provided. The bags may be used to hold any suitable product such as a diaper, an absorbent article, a cleaning product, a beauty care product, a medical product, a medical device, a food product, or other products.

The bag may be constructed of any suitable material. In one embodiment, the bag is constructed of a plastic material. In other embodiments, the bag may be constructed of other materials, such as fabric or woven or nonwoven materials. Combinations of the above materials or any other suitable material also may be used. As will be described more fully below, the access zone may be provided in any place on the bag. Further, also as described more fully below, the manner by which the access zone may be closed may vary.

The access zone provides access to the interior of the bag. More specifically, the access zone comprises an access leading to the interior of the bag and a portion enabling closure of the access. In some applications, the bag may be provided with no seal over the access opening. In other applications, the bag may be provided with a seal over the access opening. For example, in instances where the bag comprises the outer packaging of the product as sold to consumers, a seal may be provided over the access zone to protect against tampering. For example, the access zone may be covered by a perforated panel that is removed by the consumer. Alternatively, the access zone may be covered by a recloseable or removable flap or lid. In instances where the bag is an inner packing provided within an outer packaging, no seal may be provided.

Thus, for example, diapers may be sold in a plastic bag wherein the plastic bag includes two smaller bags of diapers provided therein. The smaller bags may each comprise a closeable access zone and the larger bag may have no access zone. In this situation, no seal may be provided over the closeable access zones of the smaller bags.

In some embodiments, such as shown and described with reference to FIGS. 1-12, the access zone is formed in whole or part from an elastic material. The elastic material provides a closure mechanism to the access zone. Thus, the access zone may be opened by applying an opening force thereto and is self-closing once the opening force is removed. As used herein, the terms "elastic," "elastomer," and "elastomeric" refer to a material that generally is able to extend to a strain of at least about 50% without breaking or rupturing, and is able to recover substantially to its original dimensions after the deforming force has been removed. Various materials from which the elastic material may be formed include natural or synthetic elastic materials, natural or synthetic rubber, synthetic latex, a stretch bonded laminate, a neck bonded laminate, spandex, Lycra®, an elastomeric material such as an elastomeric film or laminate, and other materials that are capable of being stretched and/or retracted.

FIGS. 1-5 illustrate an embodiment of a bag 10 having an access zone 12 comprising a slow recovery elastic. The slow recovery elastic may have, for example, an elongation of approximately 10%. In accessing the interior of the bag 10 through the access zone 12, the access zone 12 may be stretched and elongated longitudinally and/or laterally from its initial substantially compacted and untensioned state. The slow recovery elastomer may comprise, for example, from about 20% to about 70% by weight of at least one elastomeric polymer. The slow recovery elastomer exhibits a normalized unload force at 37° C. of greater than about 0.04 N/mm$^2$ and a post elongation strain of at least about 50% after 15 seconds of recovery at 22° C. The slow recovery elastomer may be prepared from a composition comprising an elastomeric polymer, optionally at least one modifying resin, and optionally one or more additives, as taught by U.S. patent application Ser. No. 11/144,508 entitled, "Absorbent Article Comprising a Slow Recovery Elastomer", filed Jun. 3, 2005. The slow recovery elastomer may be used discretely or may be joined to another material or substrate (such as a polymeric film, a nonwoven, a woven, or a scrim).

Figure 2:
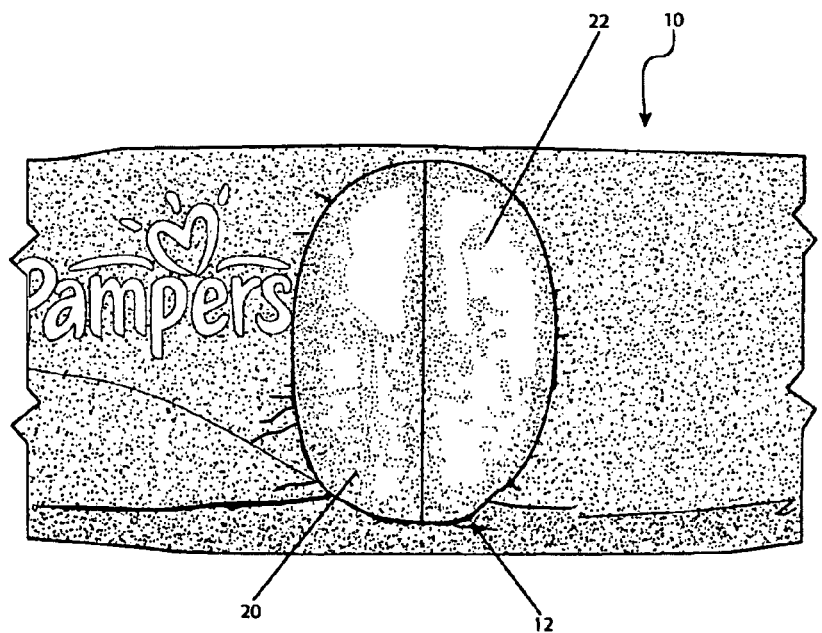
FIG. 2 illustrates a top view of the access zone of the bag of FIG. 1.
Figure 3:
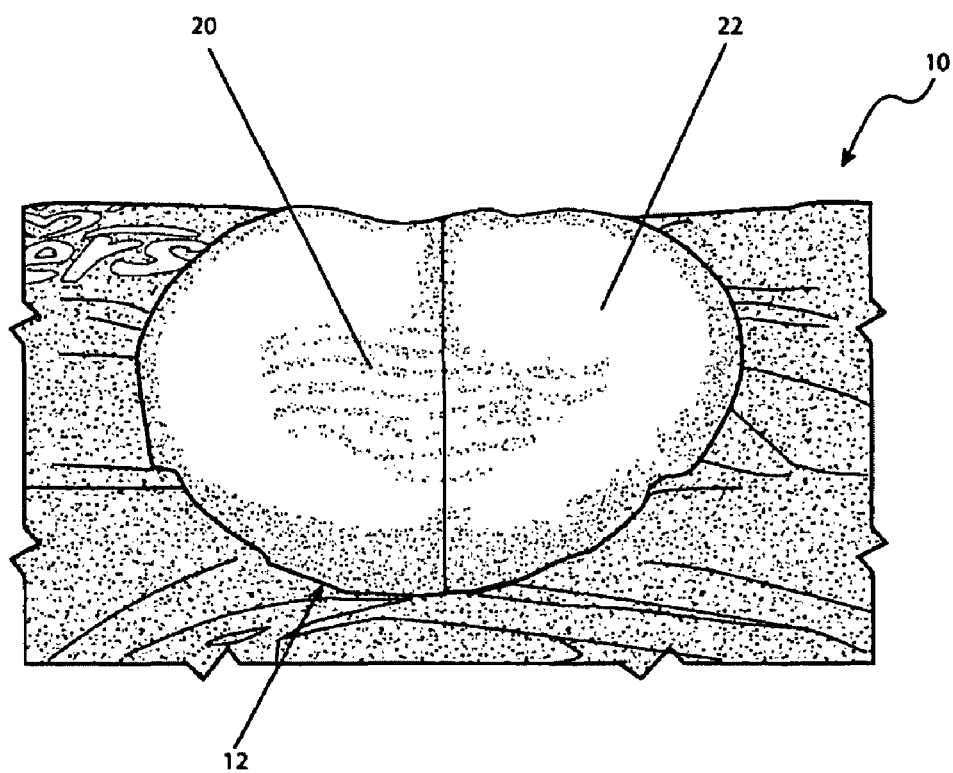
FIG. 3 illustrates a side top view of the access zone of the bag of FIG. 1.

FIG. 1 illustrates a perspective view of the bag 10 and access zone 12. FIG. 2 illustrates a top view of the access zone 12. FIG. 3 illustrates a top side view of the access zone 12. In the embodiment shown, the bag 10 is a product bag holding two rows of diapers and the access zone is provided on a side portion 14 of the bag 10. Thus, the access zone 12 can be provided along a portion of the bag having access to both rows 16 and 18 of diapers within the bag (see FIG. 4). The access zone 12 is sized to permit access into the interior of the bag 10 and removal of a product, for example a diaper, from the interior of the bag 10.

As shown in FIGS. 1-5, in one embodiment of the invention, the access zone 12 comprises a first portion 20 and a second portion 22, with one portion overlapping the other portion. The first and second portions 20, 22 may also be referred to as first and second members 20, 22. In alternative embodiments, the first and second portions 20, 22 may not be overlapping but instead may be butted up against one another. The first and second portions 20, 22 may be coupled to the bag 10 in any suitable manner and in any suitable orientation. In the embodiment shown, the first and second portions 20, 22 are coupled to the bag 10 along the interior of the bag 10. For example, an adhesive may be used to couple the first and second portions 20, 22 to the bag 10. In alternative embodiments, the first and second portions of the access zone 12 may be integral to the bag 10. For example, the material of the bag may be treated to impart enhanced extensibility to the treated region (see FIG. 18). Alternatively, the entire bag 10 or regions of the bag 10 including the first and/or second portions 20 and 22 may be formed of an elastic material.

Figure 4:
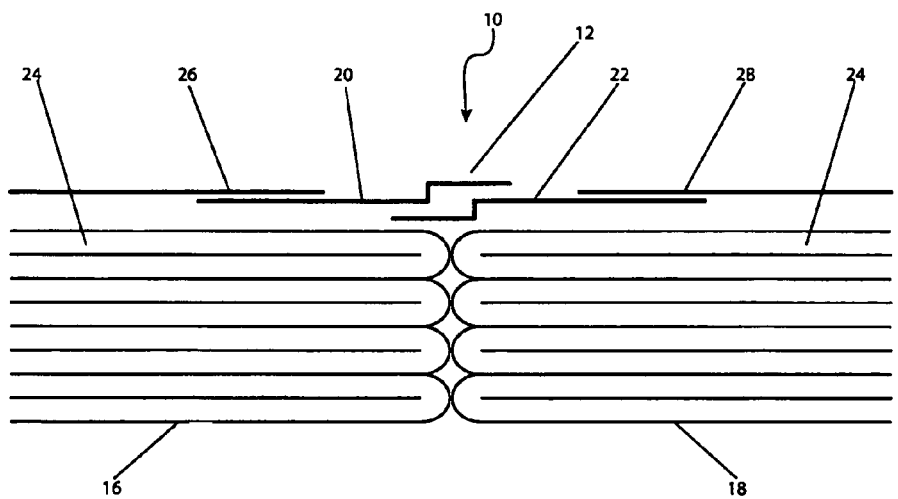
FIG. 4 illustrates a cross-sectional view of a length of the access zone of the bag of FIG. 1.
Figure 5:
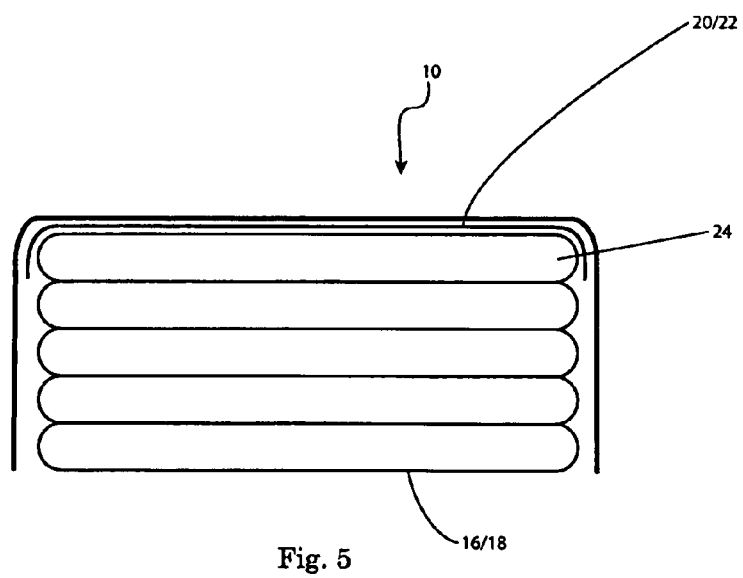
FIG. 5 illustrates a cross-sectional view of a width of the access zone of the bag of FIG. 1.

FIGS. 4 and 5 illustrate cross-sectional views of a length and width, respectively, of the access zone 12 shown in FIGS. 1-3. FIG. 4 illustrates the orientation of the diapers within the bag 10 and the overlapping nature of the first and second portions 20, 22. As shown, an end of a first or top diaper 24 from each of first and second rows of diapers 16, 18 is located beneath the access zone 12. Thus, an end of the top diaper 24 from either of the first and second rows 16, 18 can be easily accessed and handled through the access zone 12, thus permitting removal of the diaper from the bag 10 through the access zone 12. In alternative embodiments, the product within the bag 10 may be otherwise oriented with respect to the access zone 12. For example, the product may be oriented generally perpendicularly to that shown in FIGS. 4 and 5.

As can be seen in FIGS. 4 and 5, the bag 10 comprises a material, for example a plastic material, through which an access is provided. The access is thus bordered by the material of the bag. In the embodiment shown, first and second portions 20, 22 of the access zone are coupled to first and second areas 26, 28 of the bag. An adhesive, any suitable mechanical coupling, or any other suitable method may be used for the coupling. The first and second portions 20, 22 may extend the full length of the side 14 of the bag 10, as shown in FIG. 5, or may extend over only a part of the side 14 of the bag 10.

Embodiments are contemplated where the first portion 20 and the second portion 22 can be joined to one another adjacent to the overlap between the first portion 20 and the second portion 22. For example, the first portion 20 and/or the second portion 22 may comprise a pressure sensitive adhesive which allows the first portion 20 and the second portion 22 to be unattached and subsequently re-attached. Any suitable pressure sensitive adhesive known in the art may be utilized. As another example, the first portion 20 and/or the second portion 22 may comprise a mechanical fastener such as, for example, hook and loop, hook and hook, etc. As yet another example, the first portion 20 and/or the second portion 22 may comprise a macrofastener such as for example, a tab and slot, hook and eye, buttons, snaps, etc.

Figure 6:
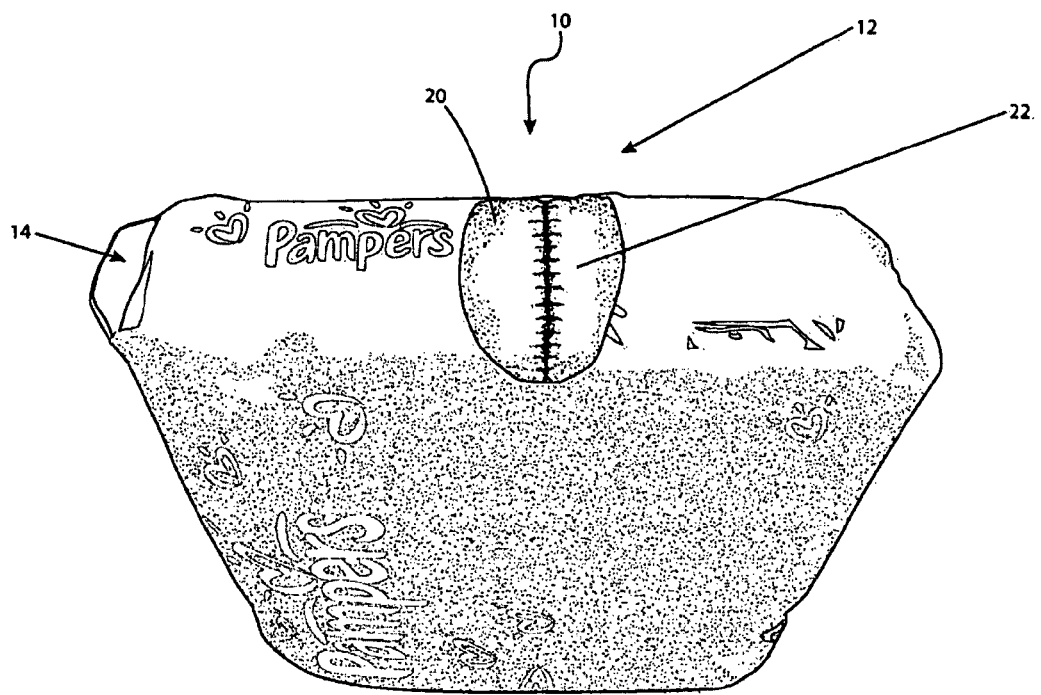
FIG. 6 illustrates a perspective view of a bag having an access zone comprising first and second overlapping portions of elastic in accordance with one embodiment of the present invention.
Figure 7:
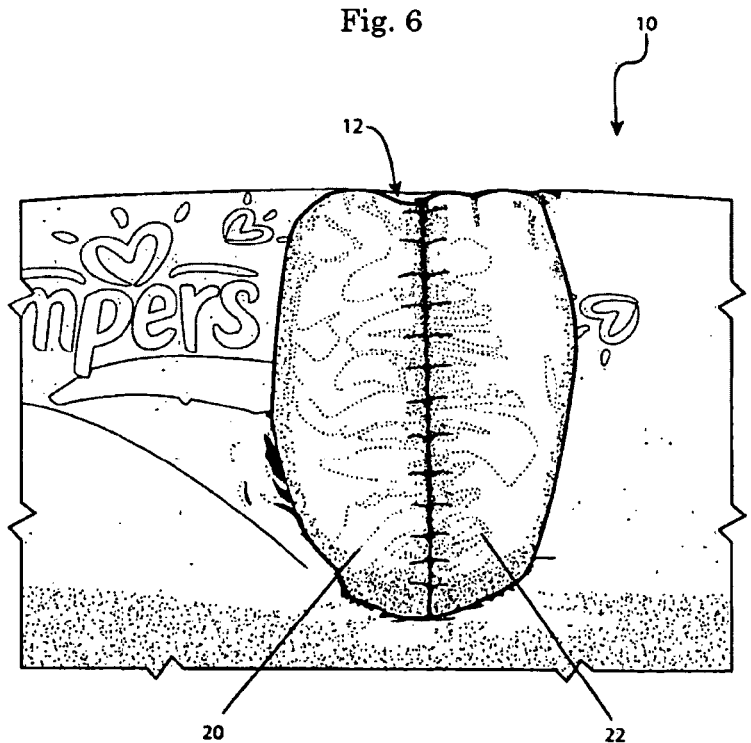
FIG. 7 illustrates a top view of the access zone of the bag of FIG. 6.
Figure 8:
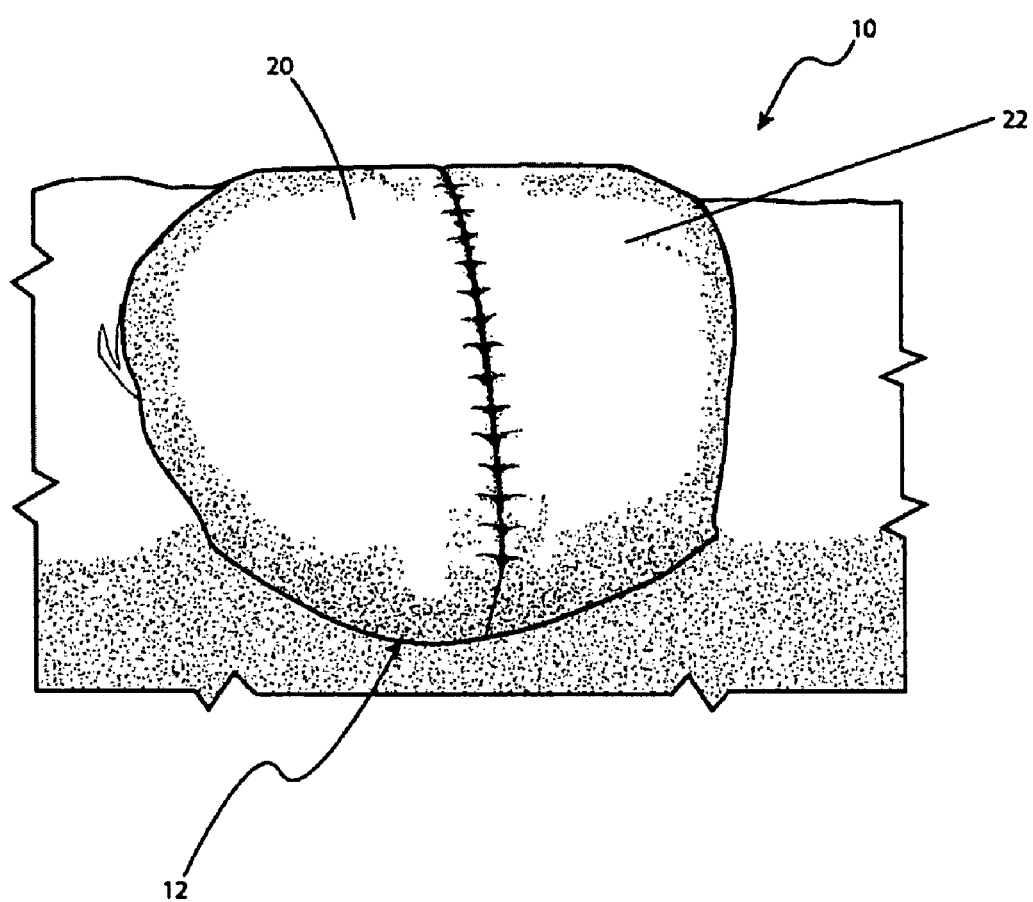
FIG. 8 illustrates a side top view of the access zone of the bag of FIG. 6.

Additionally, embodiments are contemplated where the first and second portions comprise elastic features of which at least one of the elastic features is not a slow recovery elastic. For example, FIGS. 6-10 illustrate an embodiment of a bag 10 having an access zone comprising an elastic. The elastic may have, for example, an elongation of approximately 45%. However, elastic with any suitable elongation also may be used. Examples of suitable elastics have been provided heretofore. FIG. 6 illustrates a perspective view of the bag 10 and access zone 12. FIG. 7 illustrates a top view of the access zone 12. FIG. 8 illustrates a top side view of the access zone 12. In the embodiment shown, the bag 10 is a product bag holding a single row of diapers and the access zone is provided on a side portion 14 of the bag 10. Thus, the access zone 12 is provided along a portion of the bag 10 thereby providing access to a plurality of the diapers in the single row 16 of diapers (see FIG. 9). The access zone 12 is sized to permit access into the interior of the bag and removal of a product, for example a diaper, from the interior of the bag 10. Embodiments are contemplated where the bag 10 comprises a plurality of rows of diapers. The rows of diapers can be stacked side by side and/or the rows of diapers can be stacked on top of one another.

As shown in FIGS. 6-8, the access zone 12 comprises a first portion 20 and a second portion 22, with one portion overlapping the other portion. The first and second portions 20, 22 may also be referred to as first and second members 20, 22. In alternative embodiments, the first and second portions 20, 22 may not be overlapping but instead may be butted up against one another (see FIGS. 11 and 12). The first and second portions 20, 22 may be coupled to the bag 10 in any suitable manner and in any suitable orientation. For example, in the embodiment shown, the first and second portions 20, 22 are coupled to the bag 10 along the interior of the bag 10. Also as an example, an adhesive may be used to couple the first and second portions 20, 22 to the bag 10. Any other suitable coupling mechanism, such as a mechanical device, may be used. In alternative embodiments, the first and second portions 20, 22 of the access zone 12 may be integral to the bag 10. For example, the material of the bag 10 may be treated to impart elasticity to the treated region (see FIG. 18). Alternatively, the entire bag 10 or a region of the bag 10 including the first and second portions 20, 22 may be formed of an elastic material.

Figure 9:
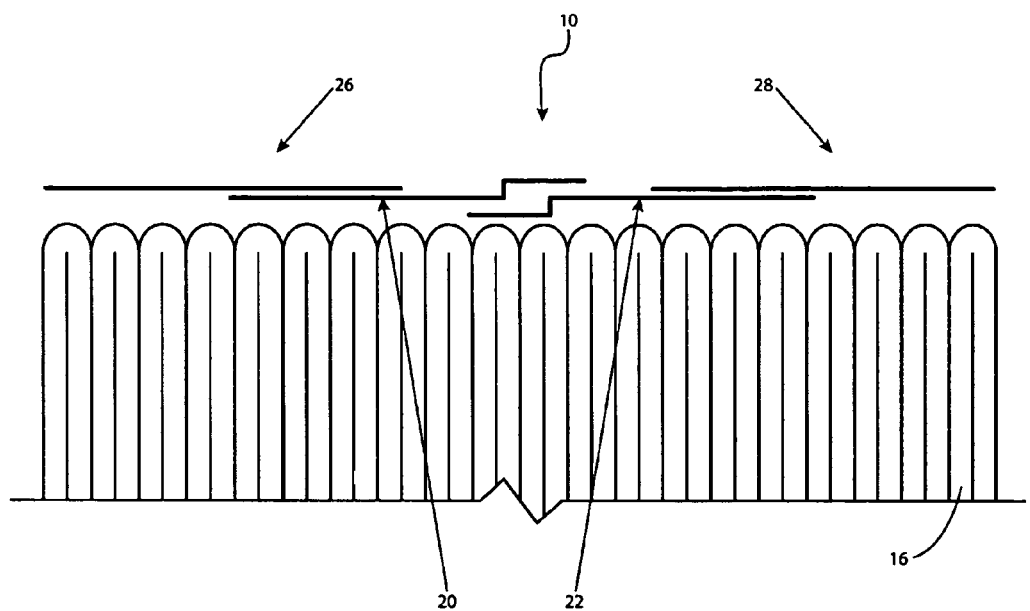
FIG. 9 illustrates a cross-sectional view of a length of the access zone of the bag of FIG. 6.
Figure 10:
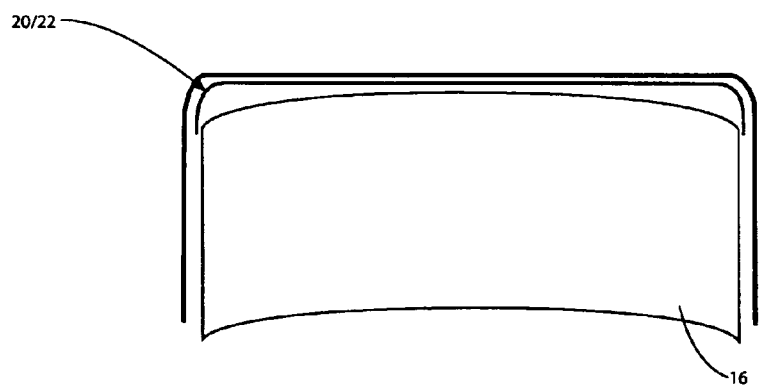
FIG. 10 illustrates a cross-sectional view of a width of the access zone of the bag of FIG. 6.

FIGS. 9 and 10 illustrate cross-sectional views of a length and width, respectively, of the access zone 12 shown in FIGS. 6-8. FIG. 9 best illustrates the orientation of the diapers within the bag for some embodiments. As shown, ends of a single row 16 of diapers abut the access zone 12. Thus, an end of the diaper is easily accessed and handled through the access zone 12, thus permitting removal of the diaper from the bag 10 through the access zone 12. In alternative embodiments, the product within the bag 10 may be otherwise oriented with respect to the access zone 12. For example, the product may be oriented generally perpendicularly to that shown.

As can be seen in FIGS. 9 and 10, the bag 10 comprises a material, for example a plastic material, through which an access is provided. The access is thus bordered by the material of the bag. In the embodiment shown, first and second portions 20, 22 of the access zone are coupled to first and second portions 26, 28 of the bag, as described above. The first and second portions 20, 22 may extend the full length of the side 14 of the bag 10, as shown in FIG. 9, or may extend over only a portion of the side 14 of the bag 10.

Figure 11:
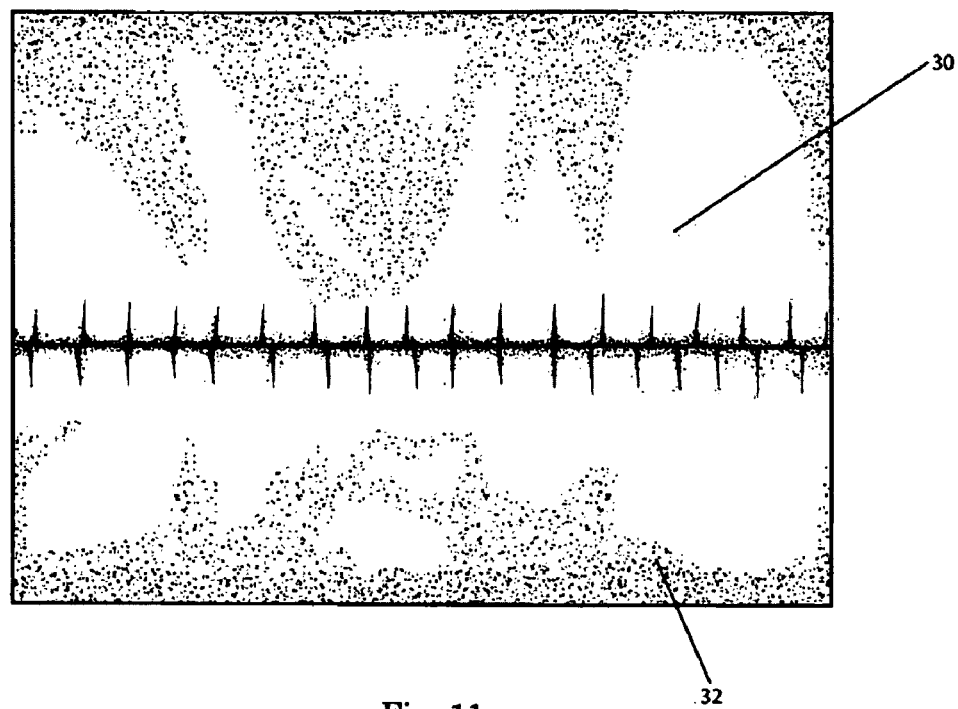
FIG. 11 illustrates a top view an access zone comprising BMI pocket elastic having first and second portions that do not overlap in accordance with one embodiment of the present invention.
Figure 12:
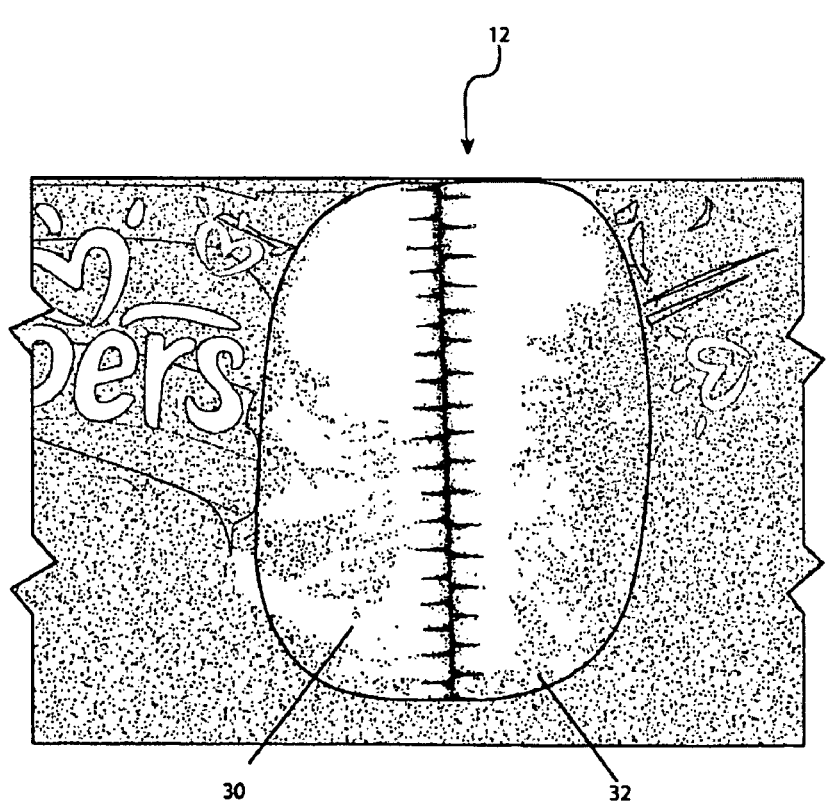
FIG. 12 illustrates a top view of the access zone of FIG. 11 presented on a bag.

FIGS. 11 and 12 illustrate an access zone 12 comprising an elastic similar to that shown in FIGS. 6-8. The access zone comprises first and second portions 30, 32. The first and second portions 30, 32 of FIGS. 11 and 12 may meet end-to-end in a non-overlapping fashion. Additionally, embodiments are contemplated where the first portion 30 and/or second portion 32 comprise a slow recovery elastic as described heretofore.

In some embodiments, such as shown and described with reference to FIGS. 13-16, the access zone 12 includes a closure mechanism such as one or more elastic bands provided within channels of another material. The access zone 12 may thus be provided integrally with the bag 10 such that the elastic bands are provided within the material of the bag 10. Any contracting or contractable material, including elastic bands or a string that may be tightened, may be used.

Figure 13:
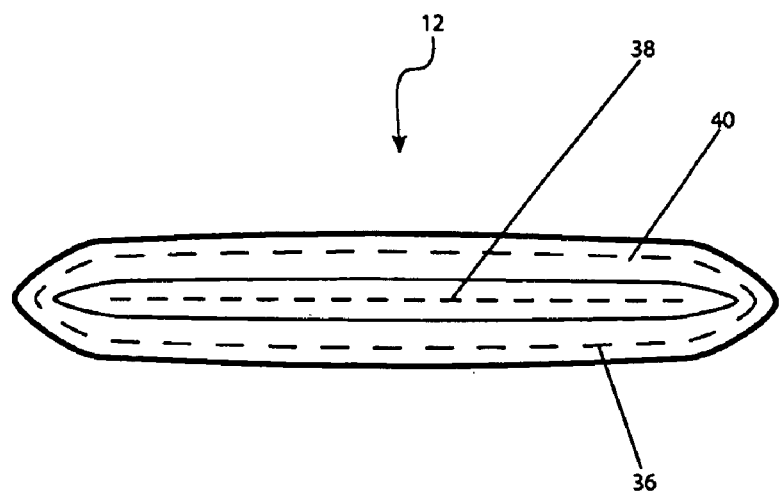
FIG. 13 illustrates a diagram of an access zone comprising an elastic band in a channel in accordance with one embodiment of the present invention.
Figure 14:
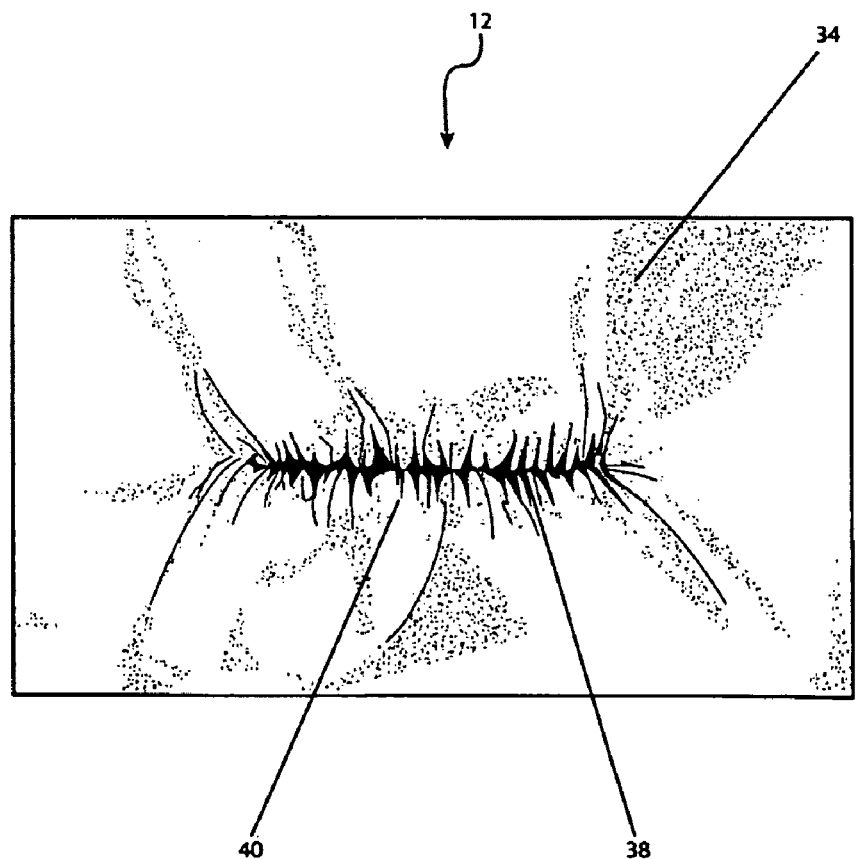
FIG. 14 illustrates a top view of an access zone comprising an elastic band in a channel in accordance with one embodiment of the present invention.

FIGS. 13 and 14 illustrate an access zone 12 comprising a non-elastic material 34 having a single elastic band 36 provided therein. Thus, for example, the access zone 12 may comprise a plastic or poly material 34. A slit opening 38 is provided generally central to the access zone 12. A channel 40 is provided around the slit opening 38. The elastic band 36 is provided within the channel 40. Thus, the elastic band 36 provides elasticized closeability to the slit opening 38. In some embodiments, the elastic band 36 can be pre-strained prior to being disposed within the channel such that rugosities are formed in the non-elastic material 34 in the relaxed state.

Figure 15:
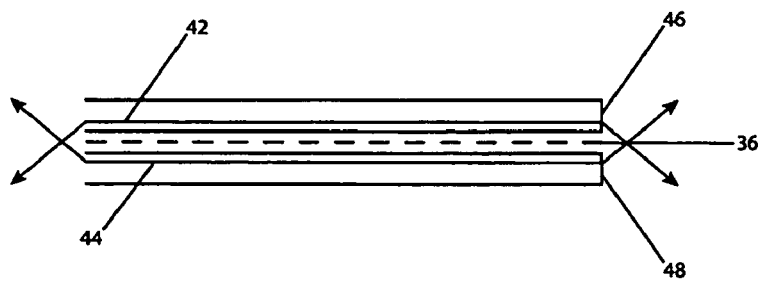
FIG. 15 illustrates a diagram of an access zone comprising elastic bands in poly channels in accordance with one embodiment of the present invention.
Figure 16:
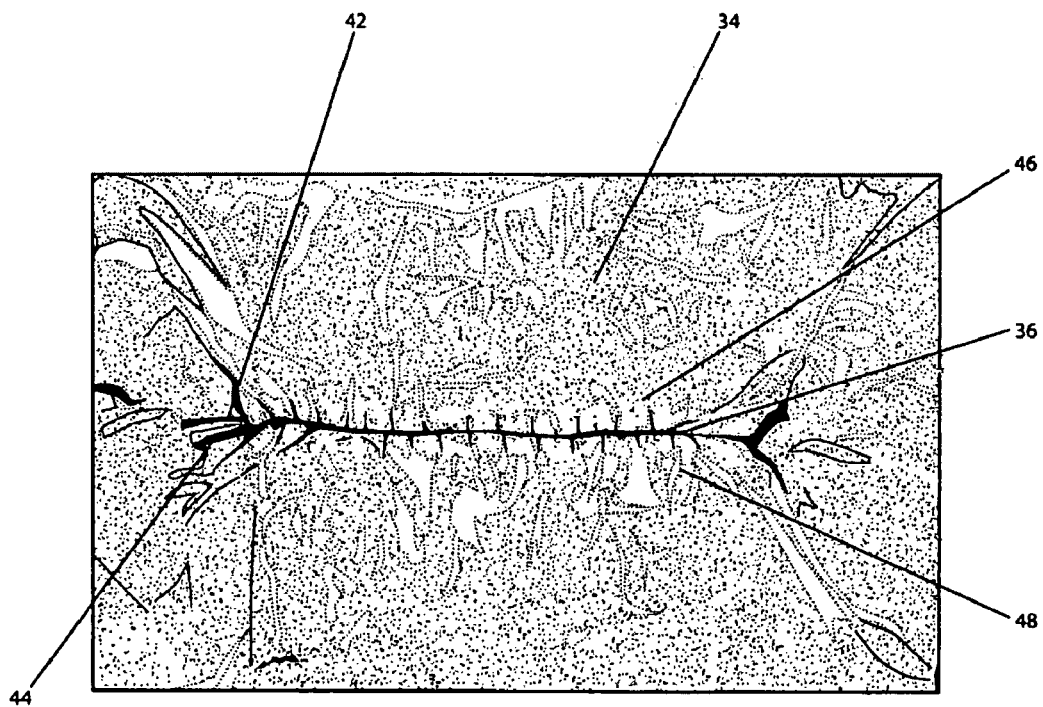
FIG. 16 illustrates a top view of an access zone comprising elastic bands in corresponding channels in accordance with one embodiment of the present invention.

FIGS. 15 and 16 illustrate an access zone 12 comprising a non-elastic material 34 having two elastic bands 42, 44 provided therein. In some embodiments, the non-elastic material 34 may comprise a plastic or poly material 34. A slit opening 38 can be provided generally central to the access zone 12. In some embodiments, a first channel 46 and a second channel 48 can be provided adjacent to the slit opening 38. First and second elastic bands 42, 44 can be provided within the first and second channels 46, 48, respectively. The bands 42, 44 can overlap one another and can be pulled outwardly at their ends to create tension into the slit opening 36. Thus, the elastic bands 42, 44 can provide elasticized closeability to the slit opening 36.

One benefit of the access zones 12 discussed heretofore is that upon release of any applied tension to the first portion and/or the second portion, the access zone 12 can automatically self close. Additionally, depending on the type of elastic member utilized, e.g., a slow recovery elastic or a conventional elastic, e.g, Lycra®, the performance of the access zone 12 can differ. For example, utilization of a slow recovery elastic may cause the access zone 12 to stay in an open state for a brief period of time even after tension previously applied to the first and/or the second portion is removed. In contrast, utilization of a conventional elastic, e.g., Lycra®, may cause the access zone 12 to close almost immediately after tension previously applied to the first portion and/or the second portion is removed.

The first portion and/or second portion of the present invention may comprise any suitable material known in the art. For example, in some embodiments, the first portion and/or the second portion may comprise a plastic material such as polypropylene. As another example, the first portion and/or the second portion may comprise a nonwoven material. As yet another example, the first portion and/or the second portion may comprise a laminate which includes a substrate and an elastic element. As yet another example, the first portion and/or the second portion may comprise a laminate which includes an elastic element which is sandwiched between two substrates. Any suitable elastic element known in the art, including slow recovery elastics may be utilized. Additionally, any suitable substrate known in the art may be utilized, e.g., a nonwoven.

Figure 17:
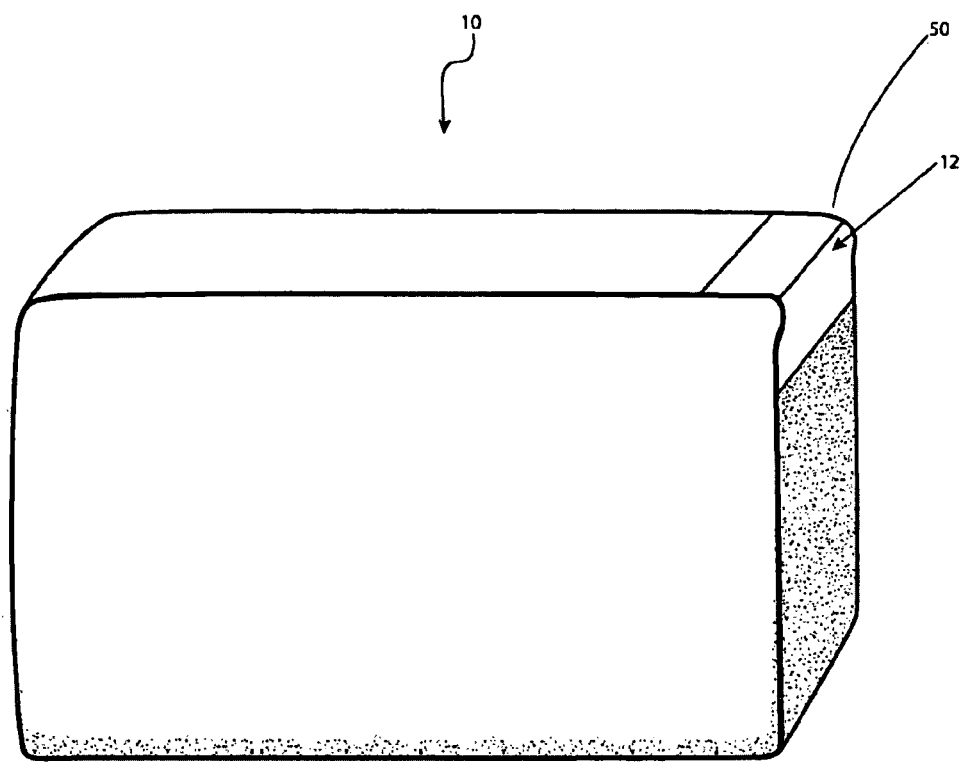
FIG. 17 illustrates a perspective view of a bag having an access zone provided at a corner thereof in accordance with one embodiment of the present invention.

FIG. 17 illustrates a bag 10 having a closeable access zone 12 wherein the access zone 12 is provided at a corner 50 of the bag 10. Such positioning of the access zone 12 may be used with any of the embodiments of access zones discussed herein. Further, the product within the bag 10 may be oriented in any suitable manner with respect to the access zone 12.

Figure 18:
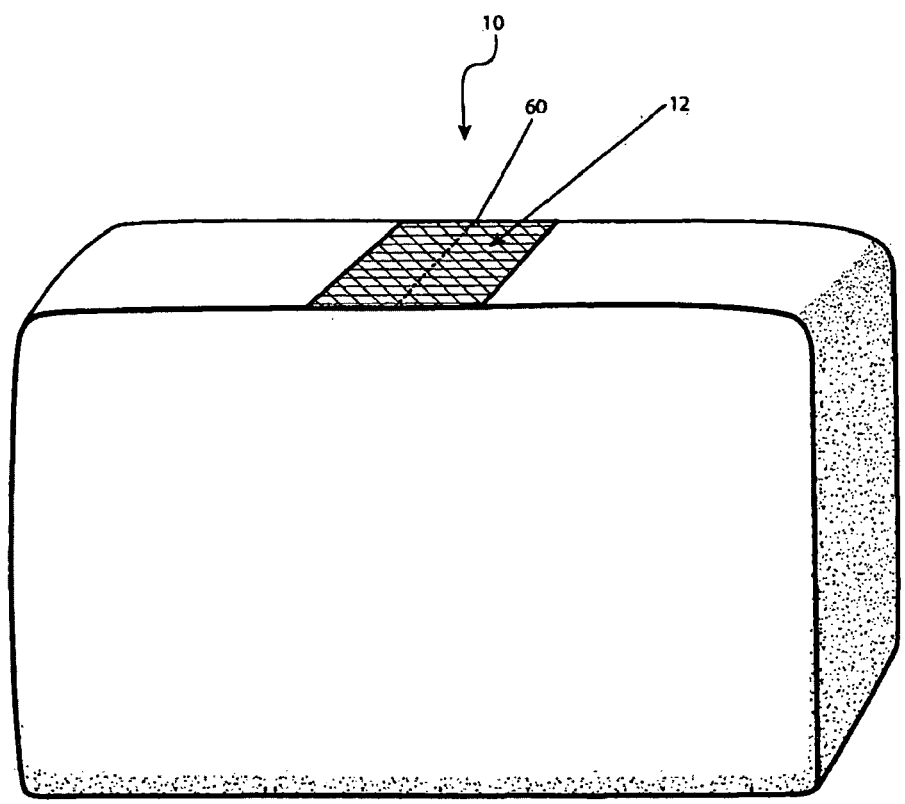
FIG. 18 illustrates a perspective view of an access zone integral with the bag in accordance with one embodiment of the present invention.

FIG. 18 illustrates a bag 10 having a closeable access zone 12 that is integral with the bag 10. More specifically, the bag 10 comprises a material, such as a poly material, where the material adjacent to the access zone 12 has been treated to enhance the extensibility of the material. Some suitable examples of treatment which can enhance the extensibility of the material include mechanical activation and SELFing. These processes are described in U.S. Pat. Nos. 4,834,741; 4,107,364; 5,143,679; 5,156,793; 5,167,897; 5,518,801; 5,650,214; 5,518,801; 6,114,263; 6,605,172; and 6,667,0521.

In the embodiment of FIG. 18, a perforation 60 is provided generally central to the access zone 12. The perforation 60 is torn by the consumer after purchase of the bag 10 to enable access to the product contained within the bag 10. Where a perforation 60 is provided, generally no further cover may be provided over the access zone 12.

In alternative embodiments, the access zone may not include an elastic portion. Thus, for example, the access zone may comprise an opening in the bag, the opening being closeably sealed with a material. In one embodiment, for example, the material may be a plastic material having a sticky portion for sticking to the bag to close the access zone. In another embodiment, the material may be a plastic material having a Velcro portion, a complementary Velcro portion being provided on the bag. Thus, the Velcro portions may be mated to close the access zone. Zippers, zip seals, and other suitable closure mechanisms also may be used. Thus, generally, the access zone may comprise an opening in the bag with a lid that may be used to close the access zone.

Figure 19:
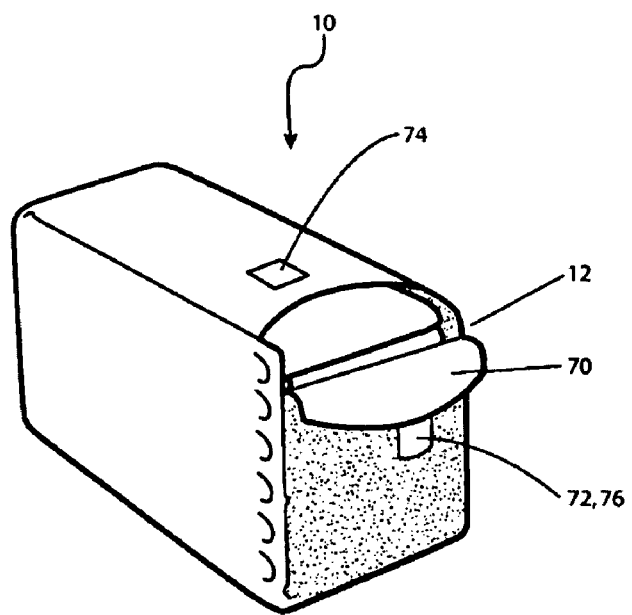
FIG. 19 illustrates a perspective view of a bag having an access zone comprising a flap, the bag being in a closed configuration, in accordance with one embodiment of the present invention.
Figure 20:
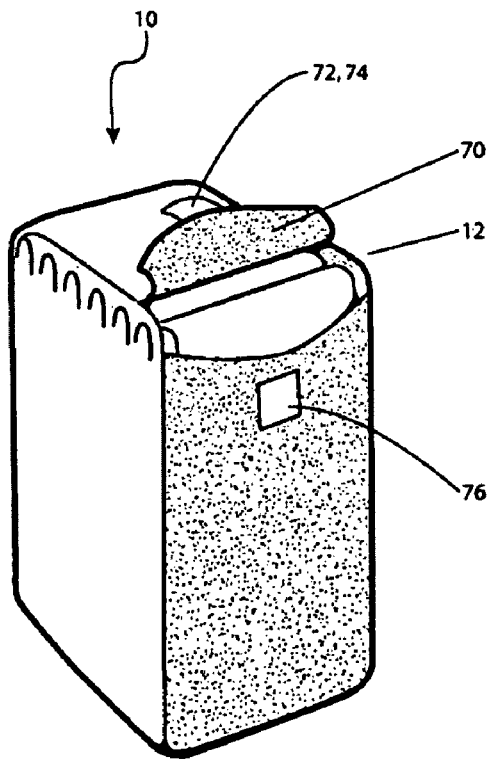
FIG. 20 illustrates a perspective view of the bag of FIG. 19 in an opened configuration.

FIGS. 19 and 20 illustrate an embodiment of a bag having a closeable access zone wherein the access zone is closeable via a tape or suitable material. In some embodiments, the bag 10 may be a poly bag or a carton such as a cardboard carton. As shown, the access zone 12 can be provided at a corner of the bag 10. Alternatively, the access zone 12 may be provided along a side of the bag 10 or at another suitable location on the bag 10. For each embodiment of the present invention, the access zone 12 may be provided at any suitable location on the bag 10. The access zone is a flap 70 that may be moved between a closed configuration, shown in FIG. 19, and an opened configuration, shown in FIG. 20. A tape 72 or other sealant material is provided on the flap 70. Corresponding tabs 74, 76 for receiving the tape 72 in a releasable manner are provided for the closed configuration (tab 76) and the opened configuration (tab 74). The tape may be formed of any suitable material such as hook and loop, adhesives, cohesives, or others. In the embodiment of FIGS. 19 and 20, the access zone 12 may be maintained in the opened configuration by affixing the tape 72 to the open tab 74 and may be maintained in the closed configuration by affixing the tape 72 to the close tab 76.

Figure 21:
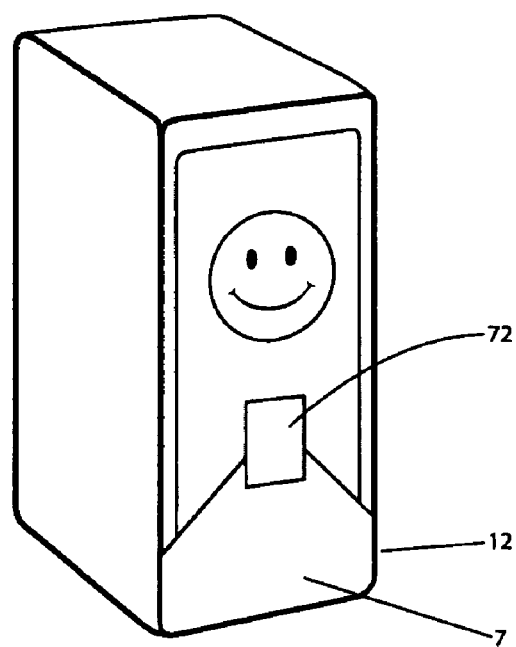
FIG. 21 illustrates a perspective view of a bag having an access zone comprising a flap, the bag being in a closed configuration, in accordance with an alternative embodiment of the present invention.
Figure 22:
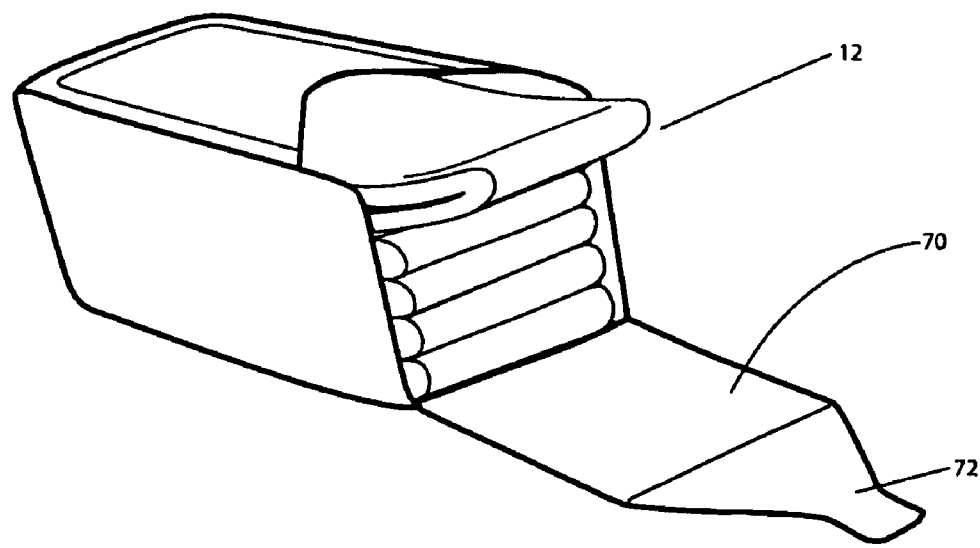
FIG. 22 illustrates a perspective view of the bag of FIG. 20 in an opened configuration.

FIGS. 21 and 20 illustrate an alternative embodiment of a bag having a closeable access zone wherein the access zone is closeable via a tape or other suitable material. As shown, the bag 10 may be a poly bag or a carton such as a cardboard carton. The access zone 12 can be provided along a top surface of the bag 10. Alternatively, the access zone may be provided along another surface of the bag 10 or along only a portion of a surface of the bag 10. The access zone is a flap 70 that may be moved between a closed configuration, shown in FIG. 21, and an opened configuration, shown in FIG. 22. A tape 72 or other sealant material is provided on the flap 70. One or more corresponding tabs for receiving the tape 72 in a releasable manner may be provided. The tape may be formed of any suitable material such as hook and loop, adhesives, cohesives, or others.

FIGS. 23-26 illustrate an embodiment of a bag 10 with a closeable access zone comprising a recloseable seam. In the embodiments shown, the bags further include handle portions and are particularly suited for carriage or travel.

Figure 23:
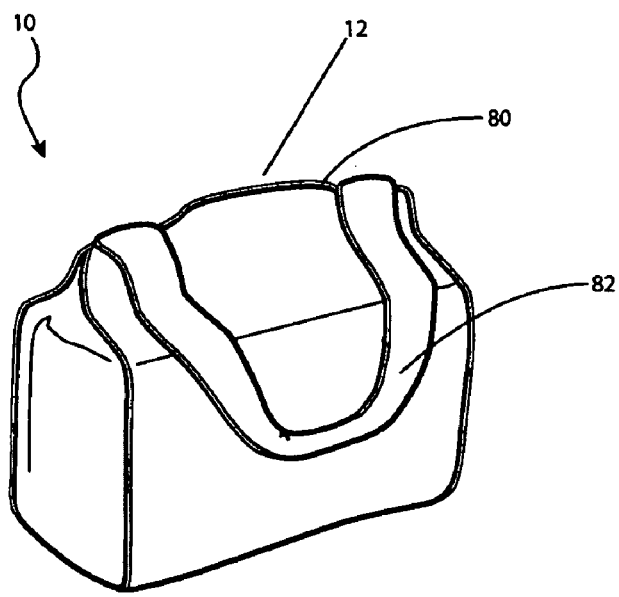
FIG. 23 illustrates a perspective view of a bag having an access zone comprising a closeable seam, the bag being in a closed configuration, in accordance with one embodiment of the present invention.
Figure 24:
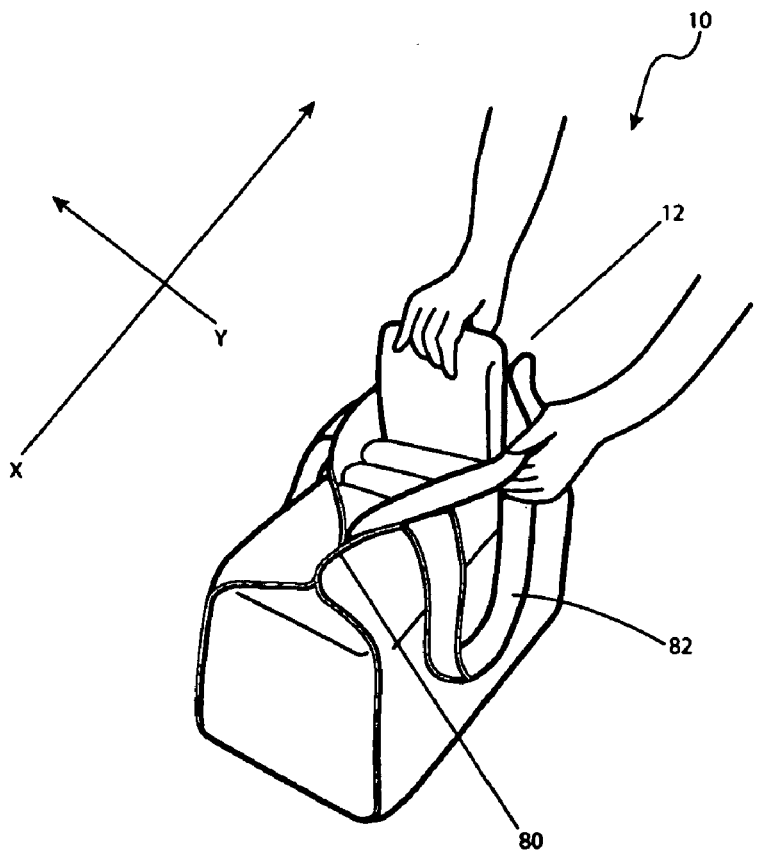
FIG. 24 illustrates a perspective view of the bag of FIG. 23 in an opened configuration.

FIGS. 23 and 24 illustrate a bag 10 having an access zone 12 along a top seam thereof, the access zone 12 being openable along two axes (x, y). The access zone 12 includes a recloseable seam 80 along one of these axes. As shown, the recloseable seam 80 is provided along the x-axis. The recloseable seam may comprise a zipper, an adhesive along the seam, a cohesive along the seam, or any other suitable releasable coupling. The bag 10 further includes handles 82 for carriage of the bag 10. FIG. 23 illustrates the bag 10 in a closed configuration. FIG. 24 illustrates the bag 10 in an open configuration.

Figure 25:
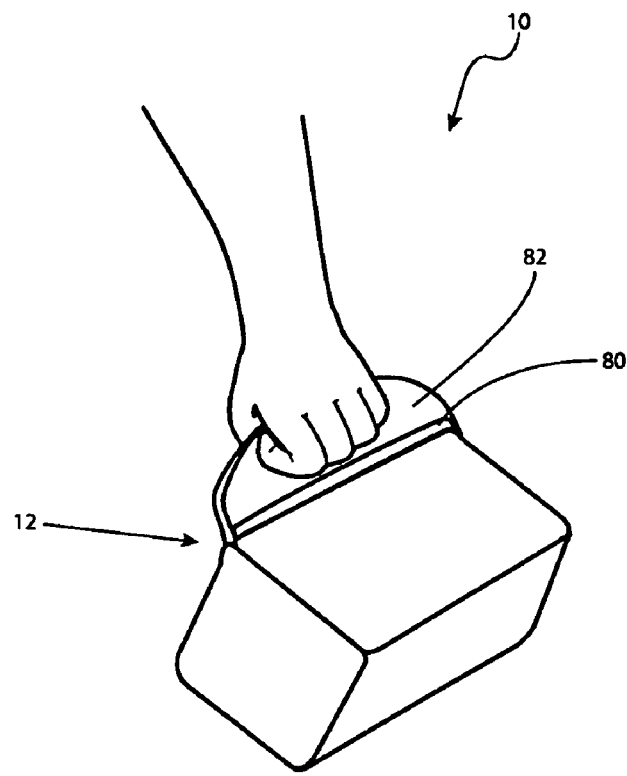
FIG. 25 illustrates a perspective view of a bag having an access zone comprising a closeable seam, the bag being in a closed configuration, in accordance with an alternative embodiment of the present invention.
}
Figure 26:
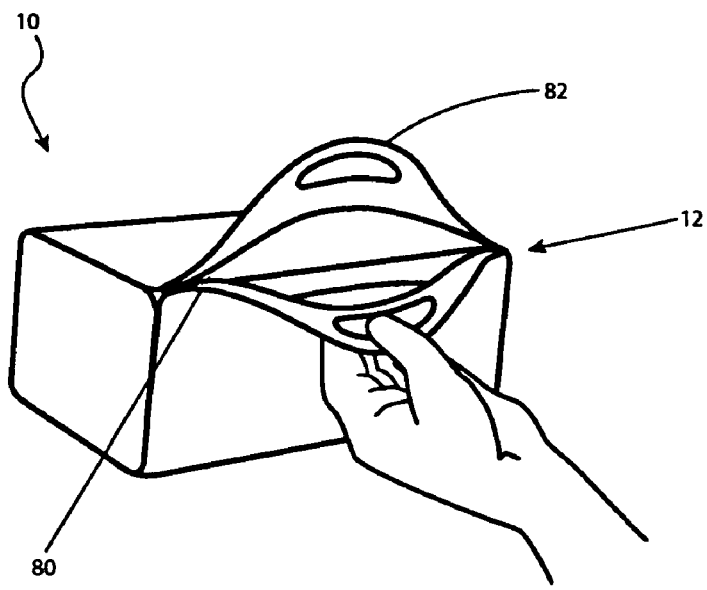
FIG. 26 illustrates a perspective view of the bag of FIG. 25 in an opened configuration.

FIGS. 25 and 26 illustrate an alternative embodiment of a bag 10 having an access zone 12 along a top seam thereof, the access zone 12. The recloseable seam may comprise a zipper, an adhesive along the seam, a cohesive along the seam, or other releasable coupling. The bag 10 further includes handles 82 for carriage of the bag 10. The handles 82 may be configured for coupling together. For example, the handles 82 may include an adhesive. FIG. 25 illustrates the bag 10 in a closed configuration. FIG. 26 illustrates the bag 10 in an open configuration.

Thus, a bag with a closeable access zone is provided. The access zone provided access to the interior of the bag to enable, for example, removal of product from the bag. The closeability of the access zone deters infiltration of contaminants into the bag. Thus, secondary storage for the products of the bag is not necessary after access to the interior of the bag.

Whether the access zones of the bags described heretofore are self closing or are closeable, as the bags are emptied, deformation of the access zone can occur. Deformation of the access zone can increase the difficulty in accessing remaining articles within the bag. Accordingly, embodiments are contemplated where the periphery of the access zone is reinforced via cardboard, for example. The reinforcement of the periphery of the access zone can reduce deformation of the access zone when the bag is less than completely full. Where the access zone is positioned on a side of the bag, the entire side of the bag can be reinforced by cardboard, for example. Where the access zone is positioned on a corner of the bag, as shown in FIG. 17, for example, the periphery of the access zone can be reinforced and/or the side on which the access zone is positioned can be reinforced. Alternatively, the entire bag may comprise a rigid material, e.g., cardboard.

In some embodiments, the periphery of the access zone can be perceptibly stiffer than the remainder of the bag. In some embodiments, a side of the bag on which the access zone is disposed may be perceptibly stiffer than the remainder of the bag.

Any suitable means of reinforcing and/or stiffening the periphery of the access zone and/or the side(s) of the bag can be utilized. An example mentioned above is cardboard. Other suitable examples include the addition of polymeric material arid the addition of filaments, e.g., plastic, carbon, and the like.

Although the invention has been described with reference to preferred embodiments, persons skilled in the art will recognize that changes may be made in form and detail without departing from the spirit and scope of the invention. For example, other closures than described herein may be used. Other closure materials other than those described herein, placed at locations on the bag other than those shown herein, also may be used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bag having a closeable access zone comprising:
   a bag for containing products; and
   an access zone provided on the bag, the access zone comprising:
      an access to the interior of the bag;
      a first portion and a second portion each joined to the bag enabling closure of the access zone;
      wherein the first portion and the second portion comprise a slow recovery elastomer, the access zone is opened upon application of tension to the first portion or the second portion, and the access zone automatically self-closes upon release of any applied tension.

2. The bag of claim 1, wherein the first portion and the second portion are overlapping.

3. The bag of claim 1, wherein the first portion and the second portion meet end-to-end.

4. The bag of claim 1, wherein the access to the interior of the bag is a slit access, first and second channels are provided along the slit access, the first portion and the second portion comprise first and second elastic bands provided within the first and second channels, respectively.

5. The bag of claim 1, wherein the first portion and the second portion are coupled to the bag using an adhesive.

6. The bag of claim 1, wherein the first portion and the second portion are integral to the bag.

7. The bag of claim 1, further comprising a seal over the access zone.

8. The bag of claim 7, wherein the seal is a perforated panel.

9. The bag of claim 1, wherein the access zone is provided along a side of the bag.

10. The bag of claim 1, wherein the access zone is provided at a corner of the bag.

11. A bag having a closeable access zone, the bag comprising:
    a plastic material;
    an access formed in the plastic material;
    an access zone wherein the access zone may be opened by applying an opening force thereto and is automatically self-closing once the opening force is removed, wherein the access zone includes a closure mechanism; and the closure mechanism comprises a first elastic portion and a second elastic portion each joined to the bag, wherein the first and second elastic portions comprise a slow recovery elastomer.

12. The bag of claim 11, wherein the plastic material is treated to provide the closure mechanism.

13. The bag of claim 11, wherein the access comprises a slit opening, wherein the access opening is bordered by a channel in the plastic material, and the closure mechanism comprises an elastic band provided within the channel.

14. The bag of claim 11, wherein the closure mechanism comprises a first elastic portion and a second elastic portion each joined to the bag, and wherein the first portion and the second portion are overlapping.

15. The bag of claim 11, wherein the closure mechanism comprises a first elastic portion and a second elastic portion each joined to the bag, and wherein the first and second elastic portions meet end-to-end.

* * * * *

UNITED STATES PATENT AND TRADEMARK OFFICE
CERTIFICATE OF CORRECTION

| | | |
|---|---|---|
| PATENT NO. | : 8,083,410 B2 | Page 1 of 1 |
| APPLICATION NO. | : 11/494253 | |
| DATED | : December 27, 2011 | |
| INVENTOR(S) | : Barry Robert Feist et al. | |

It is certified that error appears in the above-identified patent and that said Letters Patent is hereby corrected as shown below:

<u>Claim 11</u>
      Lines 45-50, delete ", wherein the access zone includes a closure mechanism; and the closure mechanism comprises a first elastic portion and a second elastic portion each joined to the bag, wherein the first and second elastic portions comprise a slow recovery elastomer." insert -- . --.

Signed and Sealed this

Thirteenth Day of November, 2012

David J. Kappos
*Director of the United States Patent and Trademark Office*

UNITED STATES PATENT AND TRADEMARK OFFICE
CERTIFICATE OF CORRECTION

PATENT NO. : 8,083,410 B2  Page 1 of 1
APPLICATION NO. : 11/494253
DATED : December 27, 2011
INVENTOR(S) : Barry Robert Feist et al.

It is certified that error appears in the above-identified patent and that said Letters Patent is hereby corrected as shown below:

Claim 11
    Column 10, Lines 45-50, delete ", wherein the access zone includes a closure mechanism; and the closure mechanism comprises a first elastic portion and a second elastic portion each joined to the bag, wherein the first and second elastic portions comprise a slow recovery elastomer." insert -- . --.

This certificate supersedes the Certificate of Correction issued November 13, 2012.

Signed and Sealed this
Eleventh Day of December, 2012

David J. Kappos
*Director of the United States Patent and Trademark Office*